(12) United States Patent
Javor

(10) Patent No.: US 7,879,375 B1
(45) Date of Patent: Feb. 1, 2011

(54) PHARMACEUTICAL COMPOSITION

(75) Inventor: Ronald David Javor, Phoenix, AZ (US)

(73) Assignee: Arizona Pharmaceuticals, LLC, Phoenix, AZ (US)

( * ) Notice: Subject to any disclaimer, the term of this patent is extended or adjusted under 35 U.S.C. 154(b) by 0 days.

(21) Appl. No.: 11/756,485

(22) Filed: May 31, 2007

Related U.S. Application Data

(60) Provisional application No. 60/815,648, filed on Jun. 23, 2006.

(51) Int. Cl.
*A61K 36/00* (2006.01)
*A61K 31/12* (2006.01)

(52) U.S. Cl. .................. 424/778; 424/779; 514/676

(58) Field of Classification Search .................. None
See application file for complete search history.

(56) References Cited

U.S. PATENT DOCUMENTS

| | | | | |
|---|---|---|---|---|
| 5,895,652 | A * | 4/1999 | Giampapa | 424/195.17 |
| 6,572,897 | B1 * | 6/2003 | Gorsek | 424/655 |
| 6,863,906 | B2 | 3/2005 | Henderson et al. | |
| 2005/0214383 | A1 * | 9/2005 | Bubnis et al. | 424/641 |
| 2005/0267091 | A1 * | 12/2005 | Berlin | 514/191 |
| 2006/0105021 | A1 * | 5/2006 | Steele et al. | 424/439 |
| 2006/0116334 | A1 * | 6/2006 | Hendrix | 514/27 |
| 2006/0281822 | A1 * | 12/2006 | Appleton | 514/709 |

OTHER PUBLICATIONS

Nina Skottova et al., "Effect of Silymarin on Serum Cholesterol in Rats", Acta Univ. Palacki. Olomuc., Fac. Med., vol. 141, 1998, pp. 87-89.
Policosanol Trial Data Summary, www.impostertrial.com/policosanol.htm, webpage.
J. Chris Bradberry, et al., "Veterans Administration Niacin Product Selection", Aug. 31, 1999, pp. 1-12, www.pbm.va.gov/reviews/niacinreview.pdf, webpage.

* cited by examiner

*Primary Examiner*—Christopher R. Tate
*Assistant Examiner*—Deborah A. Davis
(74) *Attorney, Agent, or Firm*—Booth Udall, PLC

(57) ABSTRACT

A pharmaceutical composition and method for modifying levels of cholesterol is described. Implementations of a pharmaceutical composition may comprise milk thistle and one of niacin, policosanol, and both niacin and policosanol. Implementations of a pharmaceutical composition may be administered using a method for reducing total cholesterol, LDL cholesterol, and triglycerides and increasing HDL cholesterol levels in a human or animal. The method may include the step of administering a pharmaceutically effective amount of a pharmaceutical composition that includes milk thistle and one of niacin, policosanol, and both niacin and policosanol to a human or animal.

10 Claims, No Drawings

PHARMACEUTICAL COMPOSITION

CROSS REFERENCE TO RELATED APPLICATIONS

This application claims priority to U.S. Provisional Patent Application to Ronald David Javor entitled "Combination of Ingredients for Enhanced Cholesterol and Triglycerides Improvement and Support," Ser. No. 60/815,648, filed Jul. 19, 2006, the disclosure of which is hereby incorporated entirely herein by reference.

BACKGROUND

1. Technical Field

This document relates to compositions for use in modifying levels of the various forms of cholesterol in the human or animal bloodstream.

2. Background Art

Cholesterol levels in the human bloodstream pose a health concern to many people. While cholesterol itself is one of many factors, elevated cholesterol levels, particularly in the form of Low Density Lipoproteins (LDL), show a strong correlation to various forms of heart disease and stroke, including arteriosclerosis (hardening of the arteries) and heart attack. Cholesterol itself is not inherently harmful (being a key component of organs like the brain), and some forms of cholesterol, particularly High Density Lipoproteins (HDL) actually appear to help counter the negative effects of high LDL levels. Elevated levels of other forms of cholesterol like triglycerides and Lipoprotein(a) (Lp(a)) appear to also increase risk of heart disease. While genetic factors strongly govern predisposition to elevated levels for some types of cholesterol (Lp(a), for example), many people successfully utilize a combination of diet and exercise to ensure their levels of LDL and HDL are within the recommended ranges, which are calculated to minimize the risk of heart disease and stroke. When diet and exercise prove ineffective, or when immediate reduction of cholesterol levels is critical, a variety of other methods and compositions may be needed to control the various ways cholesterol is used, metabolized, absorbed, or generated by a human or animal body to regulate levels of the various types of cholesterol.

SUMMARY

In an aspect, this document features a pharmaceutical composition that may comprise milk thistle and one of niacin, policosanol, and both niacin and policosanol.

Implementations of a pharmaceutical composition may include one, all, or some of the following.

The milk thistle may be standardized to contain between about 10% and about 95% silymarin. In particular implementations, the milk thistle may be standardized to contain about 80% silymarin.

The policosanol may be selected from the group consisting of straight chain primary aliphatic alcohols from about 20 to about 36 carbons in length.

The niacin may be one of niacin, instant release niacin, extended release niacin, nicotinic acid, niacinamide, acipimox (5-methylpyrazinecarboxylic acid, 4-oxide), aluminum nicotinate, niceritrol (3-pyridinecarboxylic acid 2,2-bis[[3-pyridinylcarbonyl]oxy]methyl)-1,3-propanediyl ester, nicoclonate, nicomol (2,2,6,6-(1-hydroxycyclohexyl) tetramethyltetrakis (3-pyridinecarboxylate), inositol hexaniacinate, and oxiniacic acid (3-pyridinecarboxylic acid, 1-oxide).

A pharmaceutically acceptable additive may be included in implementations of a pharmaceutical composition where the additive is one of a carrier, excipient, binder, colorant, flavoring agent, preservative, buffer, and dilutant. The pharmaceutical composition may be in the form of a capsule, tablet, liquid, liquid suspension, vapor, gas, or powder.

The milk thistle may be administered in a dose within a range from about 0.05 g/day to about 10 g/day. The niacin may be administered in a dose within a range from about 0.1 g/day to about 30 g/day. The policosanol may be administered in a dose within a range from about 0.5 mg/day to 5000 mg/day.

The pharmaceutical composition may include milk thistle and niacin in a ratio from about 1:1 to about 1:6 by weight. The pharmaceutical composition may also include milk thistle and niacin in a ratio of about 1:2.86 by weight.

The pharmaceutical composition may include milk thistle and policosanol in a ratio from about 1:0.001 to about 1:1 by weight. The pharmaceutical composition may also include milk thistle and policosanol in a ratio of about 1:0.034 by weight.

The pharmaceutical composition may include milk thistle, niacin, and policosanol in a ratio from about 1:1 to about 1:7 by weight. The pharmaceutical composition may also include milk thistle, niacin, and policosanol in a ratio of about 1:2.89 by weight.

In particular implementations, the composition may include one of milk thistle and niacin in a ratio of about 1:2.86 by weight, milk thistle and policosanol in a ratio of about 1:0.034 by weight, and milk thistle, niacin, and policosanol in a ratio of about 1:2.89 by weight.

In another aspect, this document discloses a method of administering a pharmaceutical composition for reducing total cholesterol, LDL cholesterol, and triglycerides and increasing HDL cholesterol levels in a human or animal. The method may include the step of administering a pharmaceutically effective amount of a pharmaceutical composition that includes milk thistle and one of niacin, policosanol, and both niacin and policosanol to a human or animal.

The method may further include administering one of milk thistle in a dose within a range from about 0.05 g/day to about 10 g/day, niacin in a dose within a range from about 0.1 g/day to about 30 g/day, and policosanol in a dose within a range from about 0.5 mg/day to about 5000 mg/day. In addition, the method of administering a pharmaceutically effective amount of a pharmaceutical composition may further include the step of administering one of aspirin, acetaminophen, and ibuprofen.

The foregoing and other aspects, features, and advantages will be apparent from the DESCRIPTION, and from the CLAIMS.

DETAILED DESCRIPTION

Terminology and Definitions

In describing implementations of a pharmaceutical composition, the following terminology will be used in accordance with the definitions and explanations set out below. Notwithstanding, other terminology, definitions, and explanations may be found throughout this document as well.

As used herein, "niacin" is a term used in its broadest sense and may refer to niacin in its many different chemical forms including niacin and niacin derivatatives. Forms of niacin include, by non-limiting example: non-prescription niacin (both in immediate and extended release form), Nicolar® tablets (immediate release niacin) and Niaspan® (extended release niacin), and other prescription and non-prescription niacin sources. Forms of niacin derivatives used may include, by non-limiting example: nicotinic acid, niacinamide, acipimox (5-methylpyrazinecarboxylic acid, 4-oxide), aluminum nicotinate, niceritrol (3-pyridinecarboxylic acid 2,2-bis[[3-pyridinylcarbonyl]oxy]methyl)-1,3-propanediyl ester, nicoclonate, nicomol (2,2,6,6-(1-hydroxycyclohexyl) tetramethyltetrakis (3-pyridinecarboxylate), inositol hexaniacinate, and oxiniacic acid (3-pyridinecarboxylic acid, 1-oxide), derivatives of the foregoing, mixtures of the foregoing, or mixtures of the foregoing and their derivatives.

As used herein, "policosanol" is a term used in its broadest sense and may refer to policosanol in many different chemical forms including policosanol and policosanol derivates. The policosanol may be one of or a mixture of the straight chain primary aliphatic alcohols (saturated and/or unsaturated) from about 20 to about 36 carbons in length. Policosanol may be derived from any particular plant or synthetic source, including sugar cane, rice wax, beeswax, yams, synthesized 1-octacosanol, and other sources. Forms of policosanol used include, by non-limiting example: 1-eicosanol (C-20), 1-docosanol (C-22), 1-tetracosanol (C-24), 1-hexacosanol (C-26), 1-heptacosanol (C-27), 1-octacosanol (C-28), 1-nonacosanol (C-29), 1-triacontanol (C-30), 1-dotriacontanol (C-32), 1-tetratriacontanol (C-34), and 1-hexatriacontanol (C-36), mixtures of the foregoing, derivatives of the foregoing, and/or mixtures of the foregoing and their derivatives.

"Milk thistle" is a term used in its broadest sense and encompasses whole herb (fresh or dehydrated, including seed, flower, fruit, leaf, stem, or root portions), herbal preparations, herbal extracts, herbal mixtures and chemicals derived from the group of plants commonly known as milk thistle. The milk thistle used in implementations of a pharmaceutical composition may be derived specifically from *Silybum marianum* and its sub-species and/or varieties. In particular implementations, pharmaceutical compositions derived from *Silybum marianum* may include preparations standardized on the basis of a family of compounds known as silymarin. Implementations of a pharmaceutical composition may include milk thistle standardized to contain between about 10% and about 95% silymarin. In particular implementations, milk thistle standardized to contain about 80% silymarin may be used.

As used herein, "pharmaceutically acceptable additive or inert ingredient" is a term used in its broadest sense. Particular implementations of the pharmaceutical composition described in this document may also include a pharmaceutically acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

As used in this document "pharmaceutical" is a term used in its broadest sense and may include, by non-limiting example, prescription compositions, over-the-counter compositions, nutritional supplements, and the like.

As used in this document, "pharmaceutically effective" is a phrase used in its broadest sense, including, by non-limiting example, effective in a clinical trial, for a specific patient, or only placebo effective.

As used in this document, "Pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

As used in this document, "about" means that the numerical value(s) immediately adjacent to the word "about" may be interpreted as a range of between +/−10% of the stated value.

Overview

Pharmaceutical composition implementations described here may comprise milk thistle and niacin, milk thistle and policosanol, or a combination of milk thistle, niacin, and policosanol along with a variety of pharmaceutically acceptable additives. Implementations of a pharmaceutical composition may be used for controlling levels of the various forms of cholesterol present in humans and animals and for treating diseases such as hypercholesterolemic diseases, total cholesterol, LDL-cholesterol, LDL/HDL ratio, Lp(a), triglycerides, coronary heart disease (heart attacks and strokes), inflammation, immunoregulatory diseases, cardiovascular diseases, deep vein thrombosis, anxiety, depression and/or neurodegenerative disorders, stroke, and others. Implementations may be made using conventional procedures or other procedures described here.

Implementations of pharmaceutical compositions described in this document may be administered, by non-limiting example, in the form of one of a capsule, a cachet, a pill, a tablet, a powder, a granule, a pellet, a bead, a particle, a troche, a lozenge, a pastille, a solution, an elixir, a syrup, a liquid, a tincture, a suspension, an emulsion, a mouthwash, a spray, a drop, an ointment, a cream, a gel, a paste, a transdermal patch, a suppository, a pessary, a cream, a paste, a foam, a vapor, a gas, an inhalable gas, an inhalable powder, and combinations thereof.

Compositions/Components

As noted, this document enables the production of pharmaceutical compositions containing milk thistle. Thus, the pharmaceutical compositions hereof may be especially advantageous, as contrasted with conventional compositions, in that they may serve to reduce levels of LDLs and triglicerides and further raise levels of HDLs. In addition, these pharmaceutical compositions may reduce the side effects present when niacin is taken in large doses into the human or animal body. Notwithstanding, in some implementations, the specific effect of modification of the levels of the various forms of cholesterol may vary from significant to almost zero, depending upon the components of the composition selected and the ratios of components chosen. In addition, particular implementations of the pharmaceutical compositions described in this document may be effective in treating a wide variety of diseases, conditions, symptoms, and/or genetic defects present in humans or animals.

Formulating pharmaceutical compositions is complex—not simply a matter of mixing a few ingredients in different ratios. Rather, pharmaceutical composition formulating involves the process of selecting and admixing appropriate ingredients in the correct proportions to provide a pharmaceutical composition with specific cholesterol level modifying effects, while minimizing symptoms of potential side effects. Possible ingredients of pharmaceutical composition implementations may include, but are not limited to, the following: milk thistle and one of niacin, policosanol, and both niacin and policosanol. Pharmaceutical compositions formed from these components may provide the effects on cholesterol levels and/or side effects characteristic of the amount of the component used.

Through empirical methods, it has been determined which blends of components may need to be administered for specific levels of cholesterol reduction and/or minimization of specific side effects. Milk thistle may be administered in a dose ranging from about 0.05 g/day to about 10 g/day. Niacin may be administered in a dose ranging from about 0.1 g/day to about 30 g/day. Policosanol may be administered in a dose ranging from about 0.5 mg/day to 5000 mg/day. Implementations of a pharmaceutical composition may include milk thistle and niacin in a ratio from about 1:1 to about 1:6 by weight on a basis of milk thistle. Particular implementations may include milk thistle and niacin in a ratio of about 1:2.86 by weight on a basis of milk thistle. Implementations of a pharmaceutical composition may include milk thistle and policosanol in a ratio from about 1:0.001 to about 1:1 by weight on a basis of milk thistle. Particular implementations may include milk thistle and policosanol in a ratio of about 1:0.034 by weight on a basis of milk thistle. Implementations of a pharmaceutical composition may include milk thistle and niacin in a ratio of about 1:1 to about 1:6 by weight on a basis of milk thistle and milk thistle and policosanol in a ratio from about 1:001 to about 1:1 by weight on a basis of milk thistle. Particular implementations may include milk thistle and niacin in a ratio of about 1:2.86 by weight on a basis of milk thistle and milk thistle and policosanol in a ratio of about 1:0.034 by weight on a basis of milk thistle.

Many additional implementations of a pharmaceutical composition are possible. For the exemplary purposes of this disclosure, a pharmaceutical composition may include milk thistle and niacin in a ratio of about 1:2.86 by weight on a basis of milk thistle and milk thistle and policosanol in a ratio of about 1:0.034 by weight on a basis of milk thistle. Milk thistle may be administered in a dose of 525 mg/day, niacin may be administered in a dose of 1500 mg/day, and policosanol may be administered in a dose of 18 mg/day. The milk thistle used may be standardized to 80% silymarin, the niacin may be in the form of nicotinic acid, and the policosanol may be in the form of a mixture of long chain aliphatic alcohols derived from sugar cane wax. The pharmaceutical composition may be administered in the form of a solid tablet.

Dosage Forms

Implementations of pharmaceutical compositions may conveniently be presented in unit dosage form. Unit dosage formulations may be those containing a daily dose or unit, a daily sub-dose, or an appropriate fraction thereof, of the administered components as described herein.

A dosage unit may include milk thistle, niacin and/or policosanol. In addition, a dosage unit may include milk thistle, niacin and/or policosanol admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

Manufacture

Implementations of a pharmaceutical composition may be made using conventional or other procedures. Accordingly, although there are a variety of method implementations for producing pharmaceutical compositions, for the exemplary purposes of this disclosure, a method implementation for producing a pharmaceutical composition may include: measuring specific quantities of milk thistle, niacin and/or policosanol, and pharmaceutically acceptable additives or inert ingredients, mixing the measured quantities of milk thistle, niacin and/or policosanol, and additional pharmaceutically acceptable additives or inert ingredients, and then separating the pharmaceutical composition into discrete quantities for distribution and/or administration.

Measuring specific quantities of milk thistle, niacin and/or policosanol, and pharmaceutically acceptable additives or inert ingredients may involve any number of steps and implementing components, and measuring specific quantities of milk thistle, niacin and/or policosanol, and pharmaceutically acceptable additives or inert ingredients may be accomplished readily from this disclosure. For the exemplary purposes of this disclosure, measuring specific quantities of milk thistle, niacin and/or policosanol, and pharmaceutically acceptable additives or inert ingredients may comprise using a scale, a solid or liquid dispensing apparatus, or other measurement device capable of measuring solid mass or liquid volume to produce a desired quantity of milk thistle, niacin, and/or policosanol, and pharmaceutically acceptable ingredient.

It should be appreciated that any of the components of particular implementations of a pharmaceutical composition may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion complexation, lyophilization, melting, mixing, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of milk thistle, niacin and/or policosanol, and pharmaceutically acceptable additives or inert ingredients may involve any number of steps and implementing components, and may be accomplished readily from this disclosure. For the exemplary purposes of this disclosure, mixing the measured quantities of milk thistle, niacin and/or policosanol, and pharmaceutically acceptable additives or inert ingredients may include combining the measured quantities of milk thistle, niacin and/or policosanol, and pharmaceutically acceptable additives or inert ingredients under the influence of physical, ultrasonic, or electrostatic forces to create a desired degree of intermingling and/or chemical reaction of the milk thistle, niacin and/or policosanol and any pharmaceutically acceptable ingredients. The mixing may be accomplished when the milk thistle, niacin and/or policosanol and/or any pharmaceutically acceptable ingredients are in a solid, liquid, or semisolid state.

Separating the pharmaceutical composition into discrete quantities for distribution may involve any number of steps and implementing components, and separating the pharmaceutical composition into may be accomplished readily from this disclosure. For the exemplary purposes of this disclosure, separating the pharmaceutical composition into discrete quantities for distribution may involve utilizing a specific piece of equipment, for example, a conventional tablet forming apparatus to shape the formed composition into individual tablets, each containing a desired dose of milk thistle, niacin, and/or policosanol. The separating process may be accomplished when the pharmaceutical composition is in a solid, liquid, or semisolid state.

Those of ordinary skill in the art will be able to readily select manufacturing equipment and pharmaceutically acceptable additives or inert ingredients to manufacture implementations of a pharmaceutical composition containing milk thistle. For the exemplary purposes of this disclosure, some examples of pharmaceutically acceptable additives or inert ingredients and manufacturing process are included below, particularly those that relate to manufacture of implementations of a pharmaceutical composition in tablet form. Notwithstanding the specific examples given, it will be understood that those of ordinary skill in the art will readily appreciate how to manufacture implementations of a pharmaceutical composition according to the other methods of administration and delivery disclosed in this document.

A particular implementation of a pharmaceutical composition may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may include, for example, magnesium stearate, calcium stearate, talc, and colloidal silica.

Particular implementations of a pharmaceutical composition may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of a pharmaceutical composition to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of a pharmaceutical composition may include diluents, or any inert substances added to increase the bulk of the pharmaceutical composition to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in a pharmaceutical composition and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

Implementations of a pharmaceutical composition containing milk thistle may also be administered through use of amphipathic lipid delivery systems (such as liposomes and unilamellar vesicles), caplet systems, oral liquid systems, parenteral and/or intravenous systems, topical systems (creams, gels, transdermal patches, etc.), intranasal systems, rectal or vaginal systems, and many other delivery methods and/or systems known to those of ordinary skill in the art. Those of ordinary skill in the art will readily be able to select additional pharmaceutically acceptable additives to enable delivery of implementations of a pharmaceutical composition from the disclosure in this document.

With respect to delivery of particular implementations of a pharmaceutical composition, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, or triangular for example. The tablets may be optionally scored so that they may be separated into different dosages. They may differ greatly in size and weight depending on the amount of the pharmaceutically acceptable active agent or agents present and the intended route of administration. They are divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multiparticulate composition, a coated multiparticulate composition, an ion-exchange resin-based composition, an osmosis-based composition, or a biodegradable polymeric composition.

While manufacture of implementations of a pharmaceutical composition have been described in particular sequences of steps and/or in particular forms, it will be understood that such manufacture is not limited to the specific order of steps or forms as disclosed. Any steps or sequences of steps of manufacture of implementations of a pharmaceutical composition in any form are given as examples of possible steps or sequences of steps or potential forms and not as limitations, since many possible manufacturing processes and sequences of steps may be used to manufacture pharmaceutical composition implementations in a wide variety of forms.

Test Procedures

Standardization of milk thistle used for implementations in this document may be accomplished through a variety of conventional methods, including those disclosed in U.S. Pat. No. 6,863,906 to Henderson et al. entitled "L-ergothioneine, milk thistle, and S-adenosylmethionine for the prevention, treatment and repair of liver damage" issued Mar. 8, 2005, the disclosure of which is hereby incorporated herein by reference. A standardized extract of milk thistle is conventionally prepared by 1) taking a part of the milk thistle plant and using a solvent to create an extract of the plant, 2) performing conventional chemical tests (such as High Pressure Liquid Chromatography (HPLC)) to determine the concentration of one or all of the family of compounds known as silymarin in the extract, and 3) concentrating or diluting the resulting extract to achieve the desired silymarin concentration.

Use

Implementations of a pharmaceutical composition are particularly useful in modifying levels of cholesterol in humans and animals. However, implementations are not limited to uses relating to cholesterol level modification, or for that matter, LDL and triglyceride level reduction, increasing of HDL levels, reduction of reactions to high levels of niacin, and the like. Rather, any description relating to the foregoing is for the exemplary purposes of this disclosure. It will be understood that implementations of a pharmaceutical composition containing milk thistle may encompass a variety of uses and are not limited in their uses, such as for treating specific medical conditions, symptoms, or genetic disorders. For example, possible uses may be, by non-limiting example, controlling levels of triglycerides, improving liver function, improving sexual performance, reducing risk of heart attack and stroke, and other diagnosed and undiagnosed medical conditions, symptoms, genetic predispositions, or disorders.

In conventional preparations of pharmaceutical compositions containing niacin, "flushing," a particular side effect, has been observed in many patients. "Flushing" is a temporary increase of blood flow to the surface of the skin, causing it to be heated and red, in some cases resembling a sunburn. Without being bound to any theory, it appears that niacin causes the liver to produce a pro-inflammatory prostaglandin hormone (PGE-2), which provokes a histamine response, causing the increase in blood flow to the skin and/or the sensation of irritation. The flushing effect is generally harmless, and may actually be beneficial in some cases. However, because of the discomfort and/or change in physical appearance, most patients who are take or are prescribed niacin discontinue use after a period of time. This is unfortunate because the effectiveness of niacin on reducing levels of LDL and triglyceride cholesterol and raising levels of HDL cholesterol is well documented.

An Aug. 31, 1999 Veterans' Administration report indicates that "niacin is also the only agent that decreases lipoprotein(a) in addition to decreasing low-density lipoprotein cholesterol (LDL-C), triglycerides (TG), and increasing high-density lipoprotein cholesterol (HDL-C)." Rodney J. Gedey and Christine Chandler, "VHA PBM-Niacin Product Selection", Niacin Product Selection Workgroup, Pharmacy Benefits Management Strategic Healthcare Group, Department of Veterans Affairs (Aug. 31, 1999) available at http://www.pbm.va.gov/reviews/niacinreview.pdf, the contents of which are hereby incorporated herein by reference. The report also indicated that use of instant release niacin, while increasing the probability of patients experiencing flushing symptoms, reduced the risk and severity of liver toxicity symptoms. Niacin reduces the liver's natural production of LDL and Lp(a) cholesterol and increases blood levels of HDL cholesterol. Niacin also inhibits production of triglycerides, allowing blood levels of triglycerides to decrease. Niacin is a vitamin and available in various forms in over-the-counter preparations. Alternatives to niacins are families of drugs known as statins, resins, and fibrates, which all modify cholesterol levels through various biological pathways, producing cholesterol modifying effects Some of the side effects of these drugs can be more severe and involve other parts of the body; statins, for example, have exhibited, as a rare side effect, muscle toxicity.

The effects of policosanol on the reduction of overall cholesterol and LDL cholesterol levels have been noted in a number of studies. While the theories as to the reasons why the policosanol family of chemicals is successful in reducing LDL cholesterol levels are varied, it is clear that the effect of policosanol alone on cholesterol levels is not as large as that of niacin. Policosanol is well tolerated and has no noted side effects.

The positive effects of milk thistle on liver performance is also well documented (see U.S. Pat. No. 6,863,906 to Henderson et al. entitled "L-ergothioneine, milk thistle, and S-adenosylmethionine for the prevention, treatment and repair of liver damage" issued Mar. 8, 2005, the disclosure of which was previously incorporated by reference, for representative information). The effect of milk thistle on the liver has been described as a protective one, as studies have indicated that taking milk thistle has protected animals who ingest poisonous mushrooms from liver damage. Without being bound to any theory, it appears that milk thistle inhibits the liver's production of prostaglandin and therefore substantially reduces or eliminates the flushing effect of niacin on a patient. Accordingly, use of implementations of pharmaceutical compositions containing milk thistle and niacin, milk thistle and policosanol, and milk thistle, niacin, and policosanol may have an effect on the levels of LDL, Lp(a), triglyceride, and HDL cholesterol and may eliminates flushing in patients.

Repeated clinical studies have indicated the effectiveness of policosanol (see references summarized and cited at http://www.impostertrial.com/policosanol.htm, the disclosure of which is hereby incorporated by reference) and particularly that of niacin in the modification of cholesterol levels in humans and animals (see the numerous published studies cited by Gedey and Chandler, ibid. previously incorporated by reference, documenting the effectiveness of various forms of niacin as treatment for hypocholesterolemia, hyperlipidemia, and hypertriglyceridemia). Many forms of heart disease and stroke are related or aggravated by the presence of undesirably high or low levels of cholesterol. Accordingly, a method of treating undesirably high levels of LDL, Lp(a), and triglycerides and undesirably low levels of HDL forms of cholesterol may include administering implementations of a pharmaceutical composition containing milk thistle along with one or both of niacin and policosanol.

EXAMPLES

The following examples further illustrate, not limit, the invention.

Example 1

For the exemplary purposes of this disclosure, a pharmaceutical composition was prepared by mixing 175 mg of milk thistle, standardized to 80% silymarin; 6 mg of policosanol derived from sugar cane; and the pharmaceutically acceptable additive ingredients calcium phosphate, cellulose, stearic acid, croscarmelose cellulose, magnesium stearate, and silicon dioxide. The pharmaceutically acceptable additive ingredients were added in sufficient quantities to allow the resulting mixture to be formed into a tablet through a compression process.

Example 2

For the exemplary purposes of this disclosure, a pharmaceutical composition containing milk thistle was prepared in the manner outlined in Example 1 above, but without adding policosanol, substituting 500 mg of instant release niacin in the form of nicotinic acid instead.

Example 3

For the exemplary purposes of this disclosure, a pharmaceutical composition containing milk thistle was prepared in the manner outlined in Example 1 above and 500 mg of instant release niacin in the form of nicotinic acid was added, creating a composition containing milk thistle, policosanol, and niacin.

The invention claimed is:

1. A pharmaceutical composition comprising: milk thistle, niacin, and policosanol in a ratio of about 1:2.86:0.034 by weight; and wherein the milk thistle is adapted to reduce flushing in a patient caused by the niacin.

2. The pharmaceutical composition of claim 1, wherein the milk thistle is standardized to contain between about 10% and about 95% silymarin.

3. The pharmaceutical composition of claim 2, wherein the milk thistle is standardized to contain about 80% silymarin.

4. The pharmaceutical composition of claim 1, wherein the policosanol is selected from the group consisting of straight chain primary aliphatic alcohols from about 20 to about 36 carbons in length.

5. The pharmaceutical composition of claim 1, wherein the niacin is one of niacin, instant release niacin, extended release niacin, nicotinic acid, niacinamide, acipimox (5-methylpyrazinecarboxylic acid, 4-oxide), aluminum nicotinate, niceritrol (3-pyridinecarboxylic acid 2,2-bis[[3-pyridinylcarbonyl]oxy]methyl)-1,3-propanediyl ester, nicoclonate, nicomol (2,2,6,6-(1-hydroxycyclohexyl) tetramethyltetrakis (3-pyridinecarboxylate), inositol hexaniacinate, and oxiniacic acid (3-pyridinecarboxylic acid, 1-oxide).

6. The pharmaceutical composition of claim 1, further comprising a pharmaceutically acceptable additive, wherein the additive is one of a carrier, excipient, binder, colorant, flavoring agent, preservative, buffer, dilutant, and combinations thereof.

7. The pharmaceutical composition of claim 1, in the form of a capsule, tablet, liquid, liquid suspension, vapor, gas, or powder.

8. A method for reducing total cholesterol, LDL-cholesterol, and triglycerides and increasing HDL-cholesterol levels in a human or animal, which comprises administering a pharmaceutically effective amount of a pharmaceutical composition comprising milk thistle in a dose of about 525 mg/day, niacin in a dose of about 1500 mg/day, and policosanol in a dose of about 18 mg/day to the human or animal; and reducing flushing resulting from administering the niacin through administering the milk thistle.

9. The method of claim 8, further comprising the step of administering one of aspirin, acetaminophen, and ibuprofen.

10. The method of claim 8, further comprising preventing liver toxicity symptoms resulting from administering the niacin through administering the milk thistle.

* * * * *